(12) United States Patent
Huet De Barochez et al.

(10) Patent No.: US 6,733,782 B1
(45) Date of Patent: May 11, 2004

(54) CORE TABLET FOR CONTROLLED RELEASE OF GLICLAZIDE AFTER ORAL ADMINISTRATION

(75) Inventors: Bruno Huet De Barochez, Ingre (FR); Patrick Wuthrich, Orleans (FR); Louis Martin, Olivet (FR)

(73) Assignee: Les Laboratories Servier, Neuilly-sur-Seine (FR)

( * ) Notice: Subject to any disclaimer, the term of this patent is extended or adjusted under 35 U.S.C. 154(b) by 0 days.

(21) Appl. No.: 09/890,427
(22) PCT Filed: Oct. 15, 1999
(86) PCT No.: PCT/FR99/02520
§ 371 (c)(1),
(2), (4) Date: Jul. 31, 2001
(87) PCT Pub. No.: WO00/18373
PCT Pub. Date: Apr. 6, 2000

(30) Foreign Application Priority Data

Feb. 1, 1999 (FR) .............................................. 99 01082

(51) Int. Cl.$^7$ ............................. A61K 9/20; A61K 9/22; A61K 9/26; A61K 9/14
(52) U.S. Cl. ...................... 424/464; 424/468; 424/469; 424/470; 424/484; 424/488
(58) Field of Search ................................ 424/488, 475, 424/468, 469, 470, 458, 464, 484

(56) References Cited

U.S. PATENT DOCUMENTS 5,057,321 A * 10/1991 Edgren et al.

* cited by examiner

Primary Examiner—Thurman K. Page
Assistant Examiner—Humera N. Sheikh
(74) Attorney, Agent, or Firm—The Firm of Hueschen and Sage

(57) ABSTRACT

The invention relates to a matrix tablet for the prolonged release of gliclazide which ensures continuous and consistent release of the active ingredient after administration by the oral route, the release being insensitive to variations in the pH of the dissolution medium.

20 Claims, 5 Drawing Sheets

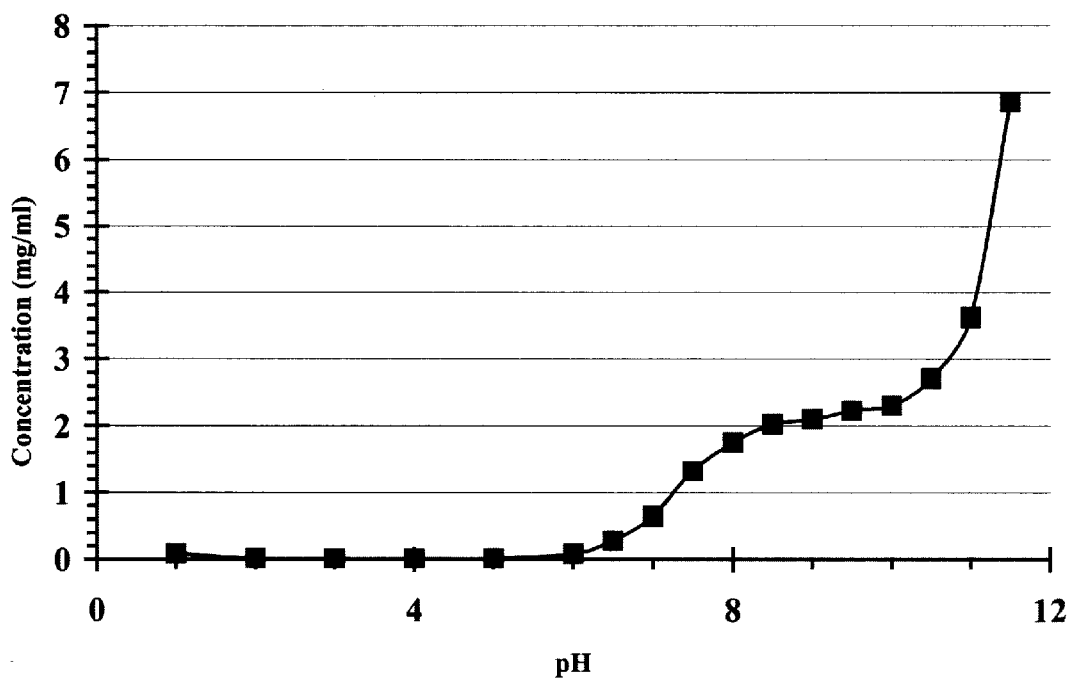
Figure 1: Solubility of the active ingredient according to pH (solubility at saturation)

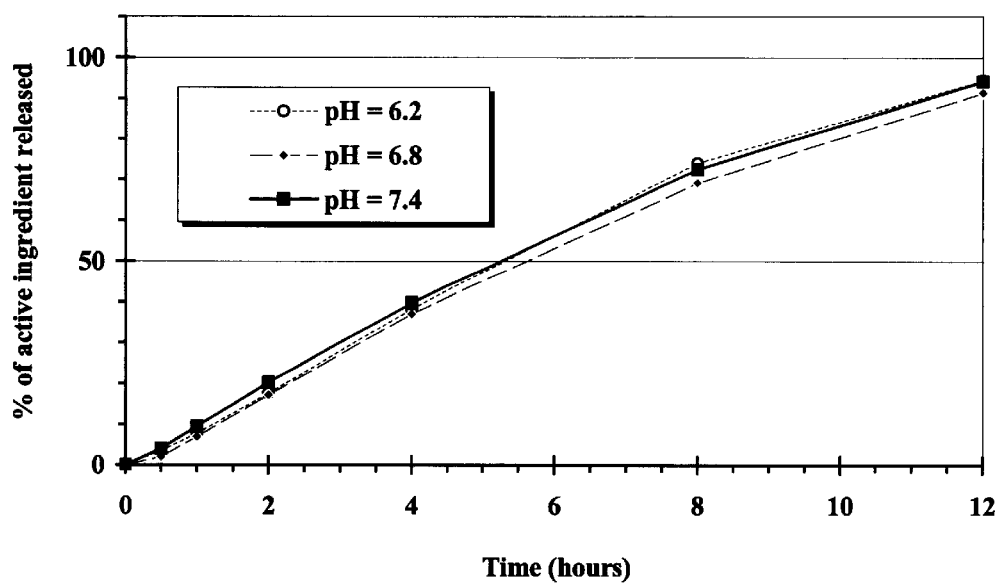
Figure 2 : Influence of the pH of the dissolution medium on the release profile of the active ingredient Figure 3 : *In vitro* dissolution kinetics of batches LP1 and LP2
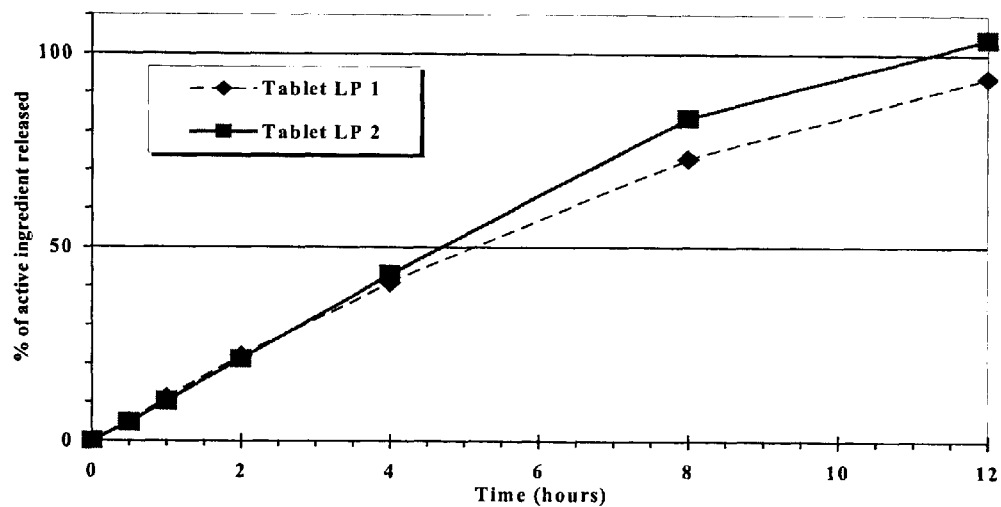
Figure 4 : *In vitro* dissolution kinetics of batches LP3 and LP4
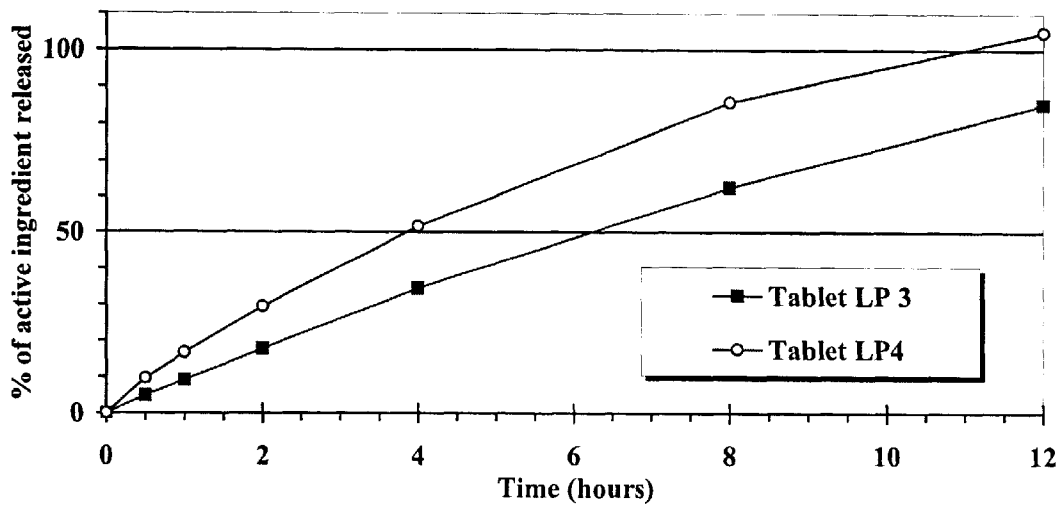

Figure 5 : *In vitro* dissolution kinetics of batches LP5 to LP7
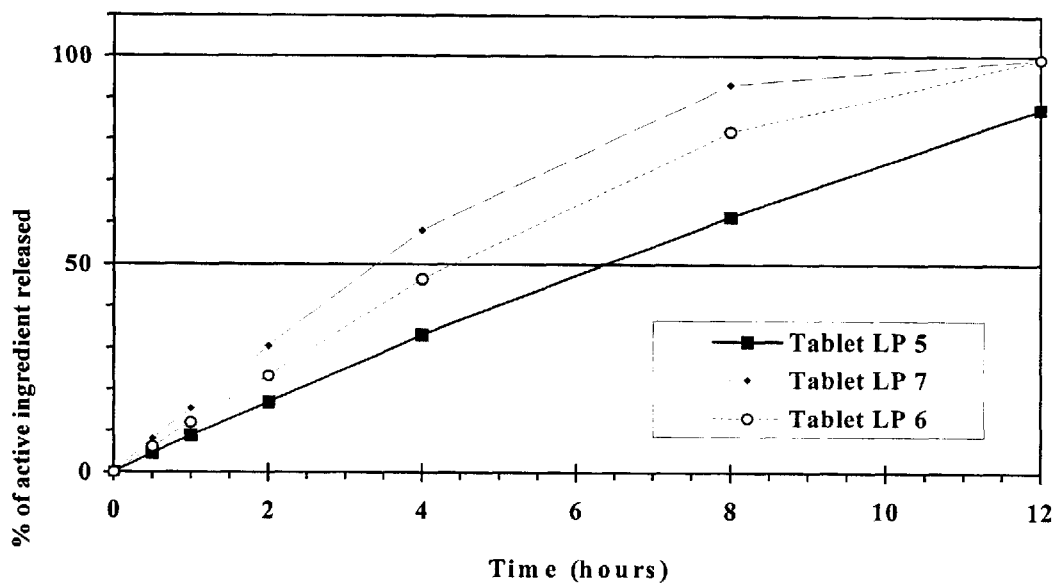
Figure 6 : Gliclazide plasma kinetics
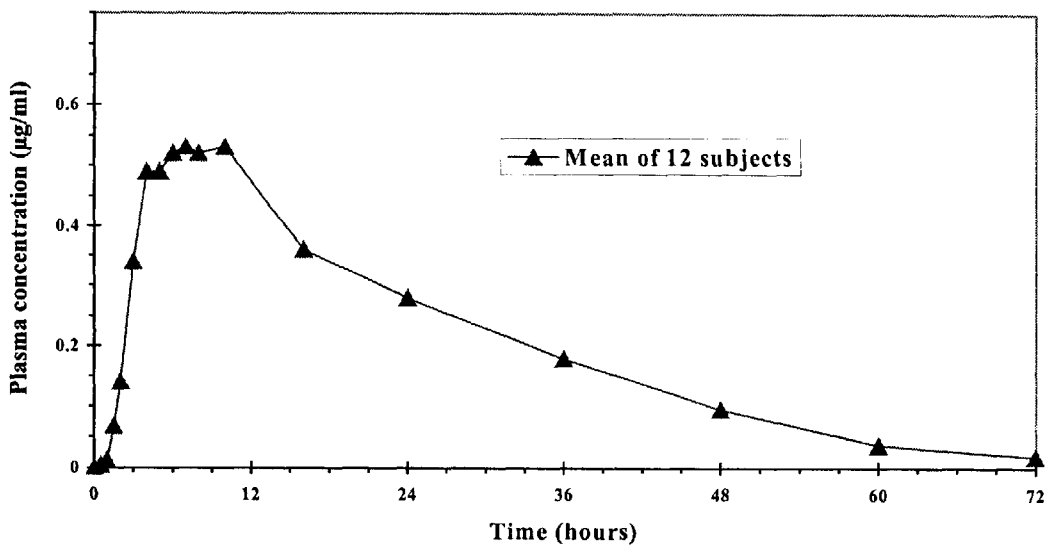

Figure 7: *In vitro* dissolution kinetics of batch LP8
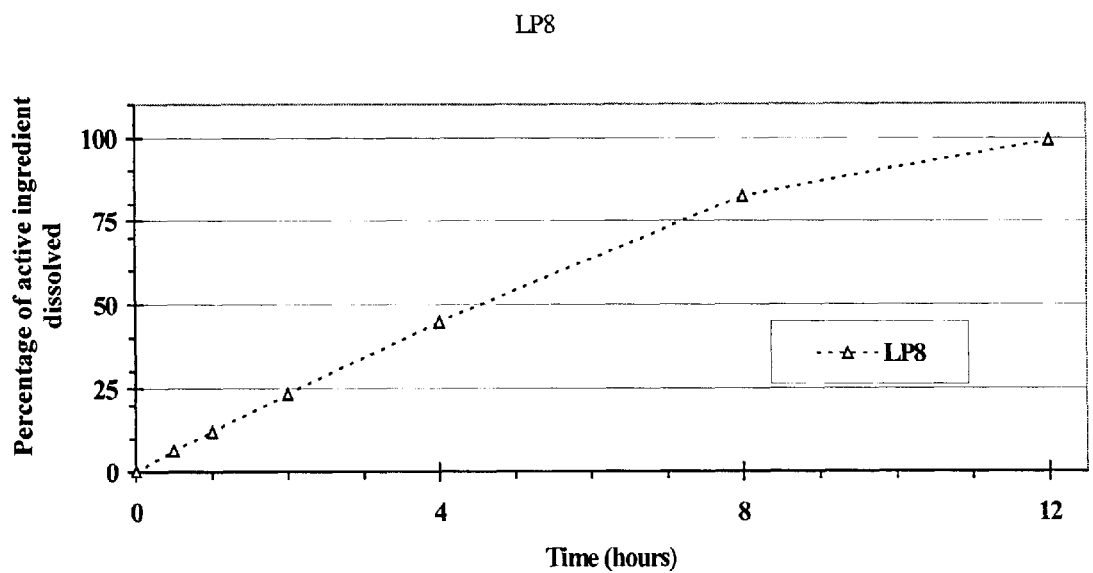

CORE TABLET FOR CONTROLLED RELEASE OF GLICLAZIDE AFTER ORAL ADMINISTRATION

This application is a 371 of PCT/FR 99/02520 filed Oct. 15, 1999

FIELD OF THE INVENTION

The present invention relates to a matrix tablet that enables the prolonged release of gliclazide, the release being insensitive to variations in the pH of the dissolution medium, and that ensures regular and continuous blood levels after absorption of the galenic form by the oral route.

PRIOR ART OF THE INVENTION

Gliclazide, a compound of formula (I):

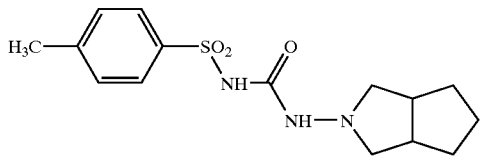

is a sulphonylurea compound having an antidiabetic property at the doses usually administered to humans.

Gliclazide has hitherto been administered by the oral route in the form of tablets containing a dose of 80 mg. The usual average prescription is two tablets per day in two administrations, but may vary from 1 to 4 tablets per day in several administrations depending upon the severity of the diabetes.

One of the aims of the present invention was to obtain an oral form that can be administered in a single daily administration. On the one hand this makes it easier for the patient to use and, on the other hand, it enables better compliance with the treatment.

Another aim of the invention was that the oral form should have prolonged release. Indeed, in certain patients an immediate-release form can result in high short-term concentrations in the blood. A prolonged-release form makes it possible for such peaks in the blood to be avoided and enables a consistent concentration in the blood to be obtained in humans. This makes it possible to reduce the undesirable effects that may occur as a result of the "peak effect", which are accompanied by hydroelectrolytic- and metabolic-type disorders associated with variations in the plasma levels of the active ingredient.

The main aim of the invention was to obtain an oral form in which the rate of release of the active ingredient is controlled and reproducible. In fact, in the current form the dissolution of the active ingredient varies greatly according to pH. This characteristic, associated with gliclazide itself, poses absorption problems for the active ingredient. The phenomenon of the solubility of the active ingredient varying according to pH is shown in FIG. 1 (attached). The solubility is very weak at acid pHs and increases as pH rises.

It was thus important, for this active ingredient, to develop a new galenic form that makes possible gliclazide release that is independent of the pH of the dissolution medium.

DISCLOSURE OF THE INVENTION

More especially, the present invention describes a hydrophilic matrix that can be administered by the oral route and that enables prolonged and controlled release of the active ingredient, gliclazide, without the pH influencing the in vitro dissolution kinetics of the said matrix.

That form for the prolonged release of gliclazide, for use in the treatment of diabetes, makes it possible to provide more consistent plasma levels and smaller $C_{max}$–$C_{min}$ variations. The rate of release must be reproducible and must be correlated with blood concentrations observed after administration.

Among the mechanisms that can be used to control the diffusion of a soluble active ingredient one principal mechanism may be selected, that being the diffusion of the active ingredient through a gel formed after the swelling of a hydrophilic polymer placed in contact with the dissolution liquid (in vitro) or with gastro-intestinal fluid (in vivo).

Many polymers have been described as being capable of enabling such a gel to be formed. The main polymers are cellulose compounds, especially cellulose ethers, such as hydroxypropyl cellulose, hydroxyethylcellulose, methylcellulose and hydroxypropyl methylcellulose and, among the various commercial grades of those ethers, those of relatively high viscosity. It should be noted that the systems described do not have the theoretical possibility of allowing a zero order to be obtained in the release kinetics equation.

The production processes currently used for the production of such matrix tablets are either direct compression, after mixing the various excipients and the active ingredient(s), or wet granulation.

The gliclazide matrix tablet described in the present invention combines in a novel manner at least one cellulose polymer compound and a glucose syrup (maize starch hydrolysate), enabling release of the active ingredient that is perfectly prolonged and controlled.

The controlled release is linear for a period of more than eight hours and is such that 50% of the total amount of gliclazide has been released between 4 and 6 hours after administration. Moreover, the matrix tablet according to the invention enables prolonged release of gliclazide that results in humans in blood levels of from 400 to 700 ng/ml 12 hours at most after a single administration by the oral route of a tablet containing a dose of 30 mg of gliclazide, and in blood levels of from 250 to 1000 ng/ml after a daily administration of a tablet containing a dose of 30 mg of gliclazide.

The unit dosage may vary according to the age and weight of the patient and the nature and severity of the diabetes. It generally ranges from 30 to 120 mg, in a single administration, for a daily treatment. The percentage of gliclazide in the matrix tablet is from 12 to 40% of the total weight of the tablet. According to an advantageous embodiment of the invention, the said tablet contains a dose of 60 mg of gliclazide. An especially preferred embodiment of the invention is the provision of tablets containing a dose of 30 mg of gliclazide. In those very advantageous examples of the invention, the unit dosage, which ranges from 30 to 120 mg, for a single daily administration, corresponds to the absorption of from 1 to 4 tablets containing a dose of 30 mg or of 1 or 2 tablets containing a dose of 60 mg. The matrix tablet as described by the Applicant on the one hand makes it possible to have an oral form that can be administered in a single daily administration and, on the other hand, surprisingly and especially advantageously, makes it possible to reduce the amount of active ingredient in each tablet without the plasma concentrations of gliclazide being modified or altered. The formulation hitherto in existence contained a dose of 80 mg of gliclazide.

The specific combination of the compounds described above also, surprisingly, makes it possible for the in vitro dissolution kinetics of the said matrix to be unaffected by the pH although the solubility of the active ingredient varies according to that same pH. This point is illustrated by FIG. 2 (attached), which shows that a matrix as formulated is insensitive to variations in pH over a range of from 6.2 to 7.4 occurring in the intestinal environment. Thus, within a pH range of from 6 to 8 corresponding to the rising part of the curve shown in FIG. 1 (attached), it can be seen that the release profile of the active ingredient at between 0 and 12 hours is the same, irrespective of the pH of the dissolution medium of the matrix tablet containing the said active ingredient.

Thus, by the characteristic combination of at least one cellulose polymer compound and a glucose syrup, the Applicant has created a hydrophilic matrix that is innovative in terms of both its composition and its function since, in particular, it enables the active ingredient that it contains, gliclazide, to be released in a prolonged and controlled manner, irrespective of the pH conditions of the dissolution medium.

The cellulose polymer compound used in that hydrophilic matrix is a high-viscosity cellulose either. Advantageously, the cellulose ether is a hydroxypropyl methylcellulose, preferably a mixture of two hydroxypropyl methylcelluloses of different viscosity. The other compound in the composition of the said matrix is a glucose syrup and, advantageously, maltodextrin is used, which is a glucose syrup having an equivalent degree of dextrose (ED) of from 1 to 20. The combination of those two types of compounds on the one hand enables a formulation to be obtained in which the release profile of the active ingredient is insensitive to variations in the pH of the dissolution medium and, on the other hand, enables perfect control of the release kinetics to be obtained. The percentage of cellulose polymer compound is from 10 to 40% of the total weight of the tablet and, according to an especially advantageous embodiment, from 16 to 26% of the total weight of the tablet. The percentage of glucose syrup is from 2 to 20% of the total weight of the tablet and, preferably, from 4 to 10% of the total weight of the tablet.

Various excipients can also be added to complete the formulation. Among the conventionally used diluents, preference is given to the use of calcium hydrogen phosphate dihydrate, which enables improved granule fluidity and improved granule compressibility to be obtained. Moreover, calcium hydrogen phosphate dihydrate is able to slow down the dissolution kinetics, that characteristic making it possible to use smaller amounts of hydroxypropyl methylcellulose to control the dissolution profile of the active ingredient. The percentage of calcium hydrogen phosphate dihydrate is from 35 to 75% of the total weight of the tablet, preferably from 45 to 60% of the total weight of the tablet. Among the lubricants there may be mentioned by way of example magnesium stearate, stearic acid, glycerol behenate and sodium benzoate and, among the flow agents, preference is given to the use of anhydrous colloidal silica.

The present invention relates also to the preparation of the matrix tablet. Wet granulation is carried out by mixing the active ingredient, glucose syrup and calcium hydrogen phosphate dihydrate, and then wetting the mixture. This first step enables the creation around the active ingredient of a hydrophilic environment that promotes its good dissolution, and also enables the provision of a unit dose that is as consistent as possible. In a second step, the granulate obtained above is mixed with the cellulose ether. If desired, the cellulose ether can be granulated directly with the active ingredient in the first step. The mixture is then lubricated by the addition of colloidal silica and magnesium stearate. The final lubricated compound is then compressed.

The following Examples illustrate the invention but do not limit it in any way.

The preparation of prolonged-release tablets that can be administered by the oral route is carried out according to the following production process:

STEP A:

Mixture of gliclazide, maltodextrin and calcium hydrogen phosphate dihydrate, followed by wetting of that mixture with purified water. The resulting wet mass is then granulated, dried and subsequently classified to obtain a granulate having physical characteristics that enable good filling of the moulds of a rapid-compression machine.

STEP B:

Mixture of the granulate obtained in Step A with hydroxypropyl methylcellulose.

STEP C:

Lubrication of the mixture obtained in Step B with colloidal silica and magnesium stearate.

STEP D:

Compression of the lubricated mixture obtained in Step C using a rotary compression machine to obtain tablets having a hardness, measured by diametric crushing, of about from 6 to 10 daN.

EXAMPLE 1

Example 1 shows the influence of maltodextrin on the in vitro release kinetics. The amount of maltodextrin ranges from 7.5 to 15 mg per tablet, thus constituting from 4 to 10% of the total weight of the tablet. The amount of hydroxypropyl methylcellulose remains constant and the amount of diluent, calcium hydrogen phosphate dihydrate, is adjusted to obtain tablets having a constant weight of 160 mg. Production is carried out according to the procedure described in Steps A to D.

TABLE 1

Unit formulation of the tablets (in mg per tablet) and characteristics

| Constituents | Batches | |
|---|---|---|
| | LP1 | LP2 |
| Gliclazide | 30 | 30 |
| Calcium hydrogen phosphate dihydrate | 87.4 | 79.9 |
| Maltodextrin (*) | 7.5 | 15 |
| Hydroxypropyl methylcellulose | 34 | 34 |
| Magnesium stearate | 0.8 | 0.8 |
| Colloidal silica | 0.32 | 0.32 |
| Final weight | 160 | 160 |
| Active ingredient dissolved at 8 h (%) | 73 | 84 |

(*) the amount of maltodextrin corresponds to 6 or 12% of the amount of granulated material (active ingredient + calcium hydrogen phosphate dihydrate + maltodextrin).

The amount of maltodextrin, at a constant hydroxypropyl methylcellulose weight, influences the release of the active ingredient for a period of more than 4 hours. The dissolution curve is linearised by increasing the amount of maltodextrin as shown in FIG. 3.

EXAMPLE 2

Example 2 shows the influence of hydroxypropyl methylcellulose on the in vitro release kinetics. The amount of hydroxypropyl methylcellulose ranges from 26 to 42 mg, thus constituting from 16 to 26% of the total weight of the tablet. Production is carried out according to the procedure described in Steps A to D.

TABLE 2

Unit formulation of the tablets (in mg per tablet)

| Constituents | Batches | |
|---|---|---|
| | LP3 | LP4 |
| Gliclazide | 30 | 30 |
| Calcium hydrogen phosphate dihydrate | 79.87 | 94.91 |
| Maltodextrin (*) | 7.01 | 7.97 |
| Hydroxypropyl methylcellulose | 42 | 26 |
| Magnesium stearate | 0.8 | 0.8 |
| Colloidal silica | 0.32 | 0.32 |
| Final weight | 160 | 160 |
| Active ingredient dissolved at 4 h (%) | 35 | 52 |

(*) the amount of maltodextrin corresponds to 6% of the amount of granulated material (active ingredient + calcium hydrogen phosphate dihydrate + maltodextrin).

The amount of hydroxypropyl methylcellulose in the hydrophilic matrix strongly influences the release of the active ingredient as shown in FIG. 4.

EXAMPLE 3

Example 3 shows the influence of the grade of hydroxypropyl methylcellulose used on the in vitro release kinetics. In each of the batches, the total weight of hydroxypropyl methylcellulose is constant and the relative amount of each of the hydroxypropyl methylcelluloses of different viscosity is varied, thereby making it possible to obtain a slow dissolution batch (LP5) and a rapid dissolution batch (LP7), compared with the reference batch (LP6).

TABLE 3

Unit formulation of the tablets (in mg)

| Constituents | Batches | | |
|---|---|---|---|
| | LP5 | LP6 | LP7 |
| Gliclazide | 30 | 30 | 30 |
| Calcium hydrogen phosphate dihydrate | 83.64 | 83.64 | 83.64 |
| Maltodextrin (*) | 11.24 | 11.24 | 11.24 |
| Hydroxypropyl methylcellulose 4000 cP | 24 | 16 | 8 |
| Hydroxypropyl methylcellulose 100 cP | 10 | 18 | 26 |
| Magnesium stearate | 0.8 | 0.8 | 0.8 |
| Colloidal silica | 0.32 | 0.32 | 0.32 |
| Final weight | 160 | 160 | 160 |
| Active ingredient dissolved at 4 h (%) | 33 | 46 | 58 |

(*) the amount of maltodextrin corresponds to 9% of the amount of granulated material (active ingredient + calcium hydrogen phosphate dihydrate + maltodextrin).

The curves of FIG. 5 show clearly that the dissolution kinetics of the active ingredient are influenced not only by the total amount of hydroxypropyl methylcellulose used in the hydrophilic matrix but also by the grade of the hydroxypropyl methylcellulose used as shown in FIG. 5.

The gliclazide plasma kinetics are measured in 12 subjects after a single administration of tablet LP6. The mean plasma concentration is given in FIG. 6.

The curve of FIG. 6 shows a matrix-type dissolution profile (continuous release of the active ingredient) with monophase plasma kinetics.

EXAMPLE 4

Example 4 shows that the in vitro release kinetics of a tablet containing a dose of 60 mg are similar to that of a tablet containing a dose of 30 mg (batch LP6) for matrix tablets containing the same doses of hydroxypropyl methylcellulose and of maltodextrin. The in vitro dissolution kinetics is shown in FIG. 7.

TABLE 4

Unit formulation of the tablets (in mg)

| Constituents | Batches LP8 |
|---|---|
| Gliclazide | 60 |
| Calcium hydrogen phosphate dihydrate | 53.64 |
| Maltodextrin | 11.24 |
| Hydroxypropyl methylcellulose | 34 |
| Anhydrous colloidal silica | 0.32 |
| Magnesium stearate | 0.8 |
| Final weight | 160 mg |
| Active ingredient dissolved at 4 h (%) | 45 |

DESCRIPTION OF THE DRAWINGS

FIG. 1 represents the phenomenon of the solubility of the active ingredient varying according to pH.

FIG. 2 represents the influence of the pH of the dissolution medium on the release profile of the active ingredient.

FIG. 3 represents the curves for the dissolution kinetics of the two formulations used in Example 1.

FIG. 4 represents the curves for the dissolution kinetics of the two formulations used in Example 2.

FIG. 5 represents the curves for the dissolution kinetics of the three formulations used in Example 3.

FIG. 6 represents the mean plasma concentration of Example 3.

FIG. 7 represents the in vitro dissolution kinetics of Example 4.

What is claimed is:

1. A Matrix tablet for the prolonged release of gliclazide, characterized in that it comprises at least the combination of a cellulose polymer compound and a glucose syrup, that combination enabling control of the prolonged release of gliclazide and enabling insensitivity of the dissolution kinetics of gliclazide to variations in pH.

2. A Gliclazide matrix tablet according to claim 1, characterized in that the cellulose polymer compound comprises at least one hydroxypropyl methylcellulose.

3. A Gliclazide matrix tablet according to claim 1, characterized in that the cellulose polymer compound comprises a mixture of two hydroxypropyl methylcelluloses of different viscosity.

4. A Gliclazide matrix tablet according to claim 1, characterized in that the cellulose polymer compound comprises a mixture of hydroxypropyl methylcellulose of viscosity 4000 cP and hydroxypropyl methylcellulose of viscosity 100 cP.

5. A Gliclazide matrix tablet according to claim 1, characterized in that the glucose syrup is maltodextrin.

6. A Gliclazide matrix tablet according to claim 1, characterized in that the percentage of cellulose polymer compound is from 10 to 40% of the total weight of the tablet.

7. A Gliclazide matrix tablet according to claim 1, characterized in that the percentage of cellulose polymer compound is from 16 to 26% of the total weight of the tablet.

8. A Gliclazide matrix tablet according to claim 1, characterized in that the percentage of glucose syrup is from 2 to 20% of the total weight of the tablet.

9. A Gliclazide matrix tablet according to claim 1, characterized in that the percentage of glucose syrup is from 4 to 10% of the total weight of the tablet.

10. A Gliclazide matrix tablet according to claim 1, characterized in that calcium hydrogen phosphate dihydrate is used as diluent.

11. A Gliclazide matrix tablet according to claim 1, characterized in that the percentage of diluent is from 35 to 75% of the total weight of the tablet.

12. A Gliclazide matrix tablet according to claim 1, characterized in that the percentage of diluent is from 45 to 60% of the total weight of the tablet.

13. A Gliclazide matrix tablet according to claim 1, characterized in that the amount of gliclazide is from 12 to 40% of the total weight of the tablet.

14. A Gliclazide matrix tablet according to claim 1, characterized in that it contains a total amount of gliclazide of 30 mg.

15. A Gliclazide matrix tablet according to claim 1, characterized in that it contains a total amount of gliclazide of 60 mg.

16. A Gliclazide matrix tablet according to claim 1, characterized in that the percentages of cellulose polymer compound and glucose syrup make possible a constant gliclazide release profile for a dissolution medium pH ranging from 6 to 8.

17. A Gliclazide matrix tablet according to claim 1, characterized in that the percentages of cellulose polymer compound and of glucose syrup make possible the release of 50% of the total amount of gliclazide by a time from 4 to 6 hours after administration.

18. A Gliclazide matrix tablet according to claim 1, characterized in that the percentages of cellulose polymer compound and of glucose syrup enable prolonged release of gliclazide that results in humans in blood levels of from 400 to 700 ng/ml 12 hours at most after a single administration of the tablet by the oral route.

19. A Process for the preparation of a matrix tablet according to claim 1, characterized in that there are used both a wet granulation technique and a direct compression technique, comprising the following steps:

STEP A:

Mixture of gliclazide, maltodextrin and calcium hydrogen phosphate dihydrate, followed by wetting of that mixture with purified water, the resulting wet mass is then granulated, dried and subsequently classified to obtain a granulate having physical characteristics that enable good filling of the moulds of a rapid-compression machine

STEP B:

Mixture of the granulate obtained in Step A with hydroxypropyl methylcellulose

STEP C:

Lubrication of the mixture obtained in Step B with colloidal silica and magnesium stearate

STEP D:

Compression of the lubricated mixture obtained in Step C using a rotary compression machine to obtain tablets having a hardness, measured by diametric crushing, of from 6 to 10 daN.

20. A Gliclazide matrix tablet according to claim 1 for use in the treatment of diabetes.

* * * * *